United States Patent [19]

Fuchs et al.

[11] 3,941,838

[45] Mar. 2, 1976

[54] PARTIAL DEHYDRATION OF CYCLOHEXANONE OXIME

[75] Inventors: Hugo Fuchs, Ludwigshafen; Rudolph Gath, Mannheim, Vogelstang; Kurt Kahr, Neustadt; Klaus Kartte, Beindersheim, all of Germany

[73] Assignee: BASF Aktiengesellschaft, Ludwigshafen (Rhine), Germany

[22] Filed: Jan. 30, 1974

[21] Appl. No.: 438,167

[30] Foreign Application Priority Data

Feb. 1, 1973   Germany............................ 2304766

[52] U.S. Cl............................................. 260/566 A
[51] Int. Cl.²..................................... C07C 131/04
[58] Field of Search................................ 260/566 A

[56] References Cited
UNITED STATES PATENTS 2,820,825   12/1958   Hillyer et al.................... 260/566 A
3,002,996   12/1961   Meier et al. ..................... 260/566 A

*Primary Examiner*—Gerald A. Schwartz
*Attorney, Agent, or Firm*—Johnston, Keil, Thompson & Shurtleff

[57] ABSTRACT

A process for the partial dehydration of cyclohexanone oxime by treatment with aqueous solutions of inorganic salts, wherein the crude cyclohexanone oxime is extracted, above its melting point, with a concentrated ammonium salt solution and/or hydroxylammonium salt solution in countercurrent in an extraction column and the salt solution is then separated from the partly dehydrated cyclohexanone oxime, reconcentrated by evaporation and recycled to the oxime dehydration process. The cyclohexanone oxime melt which has been dehydrated to water contents of about 4 to 6% by weight is treated with a heated inert gas above its melting point and the off-gas is washed to remove entrained cyclohexanone oxime.

10 Claims, 1 Drawing Figure

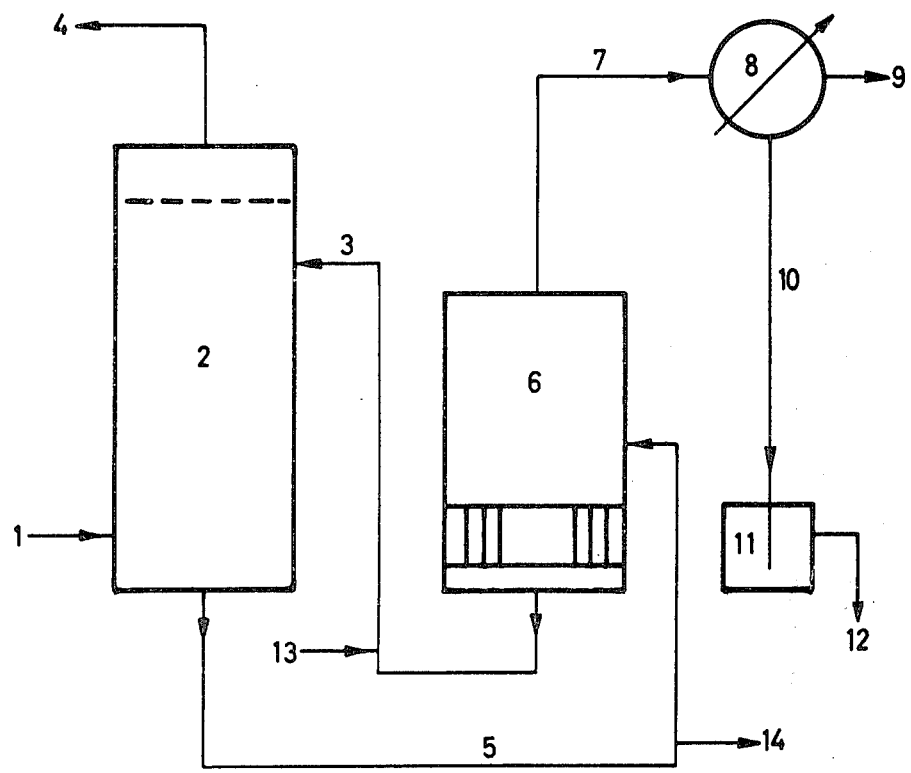

PARTIAL DEHYDRATION OF CYCLOHEXANONE OXIME

The present invention relates to a process for the partial dehydration of cyclohexanone oxime by treatment with aqueous salt solutions followed by treatment with heated gases, and is a further development of the process of U.S. Pat. Application Ser. No. 276,814.

It is known to prepare cyclohexanone oxime by oximation of cyclohexanone with a hydroxylammonium salt solution, the acid formed being neutralized with ammonia or some other base. The cyclohexanone oxime thus obtained contains water. The water content of the cyclohexanone oxime obtained by separating this two-phase mixture depends on the concentration of the salt in the aqueous phase which is separated off, and on the temperature. Accordingly, part of the water can be withdrawn from the oxime, and the water content of the oxime can be lowered, by extracting the oxime with a more concentrated salt solution than that which has been separated off. The oxime from which water has been partially withdrawn in this way is far more suitable for further conversion to caprolactam by rearrangement with strong anhydrous mineral acids such as oleum.

Whilst the conventional oximation of cyclohexanone with a hydroxylammonium sulfate solution by the Raschig process gives a cyclohexanone oxime containing 4 to 5 % by weight of moisture, oximation with a hydroxylammonium sulfate solution which has been obtained by catalytic reduction of nitric oxide with hydrogen in the presence of dilute sulfuric acid and contains less ammonium sulfate gives an oxime of about 7% by weight moisture content.

It is the object of the present invention to provide an economic method of lowering the water content of moist cyclohexanone oxime to values below 4% by weight.

This object is achieved by a process for the partial dehydration of cyclohexanone oxime by treatment with aqueous solutions of inorganic salts, wherein the crude cyclohexanone oxime is extracted, above its melting point, with concentrated ammonium salt solution and/or hydroxylammonium salt solution is countercurrent in an extraction column and the salt solution is then separated from the partly dehydrated cyclohexanone oxime, reconcentrated by evaporation and recycled to the oxime dehydration process, according to the process described in U.S. Pat. Application Ser. No. 276,814, wherein the cyclohexanone oxime which has been dehydrated to water contents of about 4 to 6% by weight is treated with a heated inert gas above its melting point and the gas is washed to remove entrained cyclohecanone oxime.

Surprisingly, it has been found that impurities do not accumulate in the recycled aqueous solution and instead even a further purification of the oxime is achieved. The residual cyclohexanone is either separated off or completely converted, and other impurities which are volatile in steam are also removed.

Particularly suitable ammonium salt solutions to use are aqueous concentrated ammonium sulfate solution and/or hydroxylammonium sulfate solutions. However, solutions of ammonium salts of other mineral acids such as, for example, phosphate or chloride solutions, can also be used. The concentrated hydroxylammonium salt solutions, which at the temperature of the molten oxime are almost saturated solutions, have the advantage that they not only extract the water and extractable impurities in the oxime but also effect a post-oximation. Thus cyclohexanone residues still present in the cyclohexanone oxime and normally accounting for up to 0.1% by weight are completely removed by oximation. Instead of using pure ammonium salts or hydroxylammonium salts, it is possible to use their mixtures such as, for example, ammonium sulfate solutions or hydroxylammonium sulfate solutions, for partial dehydration of the cyclohexanone oxime. To achieve as thorough dehydration as possible of technical cyclohexanone oxime, concentrated aqueous salt solutions, which can be almost saturated, are used. In principle, the extraction can be carried out with less concentrated salt solutions and in this way cyclohexanone oxime of any desired moisture content, up to a maximum of 9% by weight of $H_2O$, can be obtained.

The partial dehydration of the moist technical cyclohexanone oxime with the salt solutions is carried out at temperatures above the melting point of the aqueous oxime, that is to say above 65°C and below the boiling point of the salt solution. Preferably, the temperature is maintained at 75° to 95°C.

In general, the partial dehydration of the cyclohexanone oxime with the concentrated ammonium salt solutions and/or hydroxylammonium salt solutions in the first place gives cyclohexanone oxime containing 4 to 6% by weight of water if the nature and concentration of the solutions are chosen appropriately. Thus, for example, cyclohexanone oxime produced on a commercial scale and containing 7.2% by weight of water is brough to a water content of 5.0% by weight by extraction with a 48% strength by weight ammonium sulfate solution at 85°C and to a water content of 4.2% by weight by extraction with a 62% by weight hydroxylammonium sulfate solution.

The pH of the salt solutions used for the extraction of the cyclohexanone oxime should preferably be adjusted to a neutral or weakly acid value, that is to say to a value between 3 and 6. For example, the pH can be kept at about 5 when using an ammonium salt solution and at about 3 when using a hydroxylammonium salt solution.

The partial dehydration of the oxime with the salt solutions is advantageously carried out in a heated tower or a column, for example with sieve trays or rotating plates, in countercurrent, the layers being separated in the upper part of column. The partially dehydrated oxime can be withdrawn through an overflow from the upper part of the column whilst the salt solution which has only been diluted slightly issues from the lower part and is continuously passed to the evaporation stage and recycled. In the extractive dehydration, the ratio of the amount of circulating salt solution to the amount of cyclohexanone oxime introduced can vary within wide limits. Normally, more than 0.3 part by volume of the concentrated salt solution per 1 part by volume of cyclohexanone oxime is sufficient. The evaporation of the salt solution is carried out in an evaporator in which the water taken up from the oxime and the impurities which are volative in steam are distilled off so that the solution returns to the same salt concentration as before and can be reused for dehydrating the oxime. The evaporation of the salt solution is preferably carried out under slightly reduced pressure. However, it can also be carried out under atmospheric pressure or moderately increased pressure. It is advantageous to adjust the pressure so that the evaporation temperature is approximately the same as the temperature during the extractive dehydration of the oxime.

To make up, or replace, the circulating concentrated salt solution, it is possible to feed fresh ammonium salt solution and/or hydroxylammonium salt solution to the circulating system and discharge a corresponding amount of the spent solution. Amounts of up to 3% by weight, based on the oxime employed, of a fresh salt solution are sufficient for this purpose. Thus, for example, the ammonium sulfate solution produced during the oximation can be used for this purpose.

The attached FIGURE schematically shows an installation in which the partial dehydration with the concentrated salt solutions can be carried out. The molten cyclohexanone oxime, containing water, flows through pipeline 1 into the extraction column 2 and rises up through the salt solution. The phase boundary between the salt solution and the oxime forms in the upper part of the column. A concentrated salt solution is fed to the extraction column 2 through pipeline 3. The partially dehydrated oxime is withdrawn through pipeline 4 at the head of column 2. In the lower part of the column, the slightly diluted salt solution passes through pipeline 5 into distillation column 6, in which the water taken up by the oxime is again evaporated and the original salt concentration is restored. The vapors escape through pipeline 7 and are condensed in condenser 8, suction being applied through pipeline 9. The condensate is discharged through pipeline 10, receiver 11 and pipeline 12. The salt solution which has been concentrated leaves the lower part of column 6 and returns to extraction column 2 through pipeline 3. Fresh salt solution can be fed in through pipeline 13 and discharged through pipeline 14.

The cyclohexanone oxime which has been partly dehydrated by means of the concentrated salt solutions — and is, for example, discharged through pipeline 4 in the figure — is now treated, that is to say thoroughly mixed, with a heated gas. To do this, a vigorous stream of gas can be allowed to pass through a layer of the molten oxime; alternatively, the countercurrent principle is employed, advantageously in a packed tower. In such a tower, the molten oxime is preferably introduced at the head of the column and the gas is introduced in countercurrent through the lower part of the column.

The gas, which must of course be inert toward the oxime, can be air, nitrogen, argon or the like. The heated gas fed to the molten oxime is preferably at a temperature above 65° and up to about 120°C, especially from 80° to 95°C. The heated gas then keeps the oxime molten. However, it is also possible to provide additional heaters on the apparatus used.

The off-gas obtained is washed to free it from entrained oxime. In principle, the gas used for the post-drying treatment can be freed from entrained oxime after a single pass through the oxime. However, it is advantageous to recycle the gas and pass it through the oxime several times before freeing it from entrained oxime.

The ratio of the amount of oxime to gas depends on the water content of the oxime to be dehydrated and on the desired water content. It is generally 1:10 to 1:100 and especially 1:15 to 1:80.

A suitable method of freeing the off-gas from the entrained oxime is to wash it with aqueous fluids such as with hydroxylammonium salt solutions or ammonium salt solutions, especially solutions of the sulfates, of 5 to 30% by weight concentration, or with dilute sulfuric acid or water. The oxime can be recovered from the aqueous solutions resulting from the washing process, for example by extraction with inert solvents such as with cyclohexanone. In principle, it is also possible to freeze out the oxime entrained by the gas.

The process of the invention provides an economical method of lowering the water content in the oxime to below 4% by weight. Preferably, the oxime is dehydrated to water contents from 2.0 to 4.0, especially from 3.0 to 4.0, % by weight. It is not desirable to lower the water content further since in that case ammonium salts dissolved in the oxime, which may have been retained from the manufacturing process, may precipitate. At water contents below 1% by weight, the rearrangement of the cyclohexanone oxime to caprolactam, which usually follows as the next step, is also too vigorous and no longer easily controllable. In addition, the viscosity of such a mixture used for the rearrangement reaction and containing, for example, sulfuric acid, increases so greatly as to make adequate mixing uncertain.

The process of the invention is particularly economical. Using the aqueous salt solutions mentioned, the cyclohexanone oxime can only be dehydrated to about 4% by weight. Dehydration with heated gases alone is uneconomical because of the large amounts of gas required and the expensive recovery of the entrained oxime, the amounts of which are considerable under the circumstances. Using the process of the invention, a part of the water is removed from the cyclohexanone oxime with aqueous salt solutions and the remainder which requires to be removed is then removed with relatively small amounts of gas. The water content of the oxime can be readily adjusted to the desired values between 2.0 and 4.0% by weight.

The percentages mentioned in the Examples are by weight.

EXAMPLE 1

126 parts by volume of molten technical cyclohexanone oxime containing 7% of water are extracted with 30 parts by volume of a concentrated ammonium/hydroxylammonium sulfate solution containing 47% of ammonium sulfate and 10% of hydroxylammonium sulfate, at a pH of 4.9 and 80°C, in an apparatus such as that shown in the figure described above. 123 parts by volume of cyclohexanone oxime containing 4.8% of water and 0.05% of cyclohexanone are obtained at the head of the extraction column. 2.9 parts by volume of water are distilled from the circulating sulfate solution in a distillation column at 80°C and 280 mm Hg.

160 kg per hour of this molten cyclohexanone are introduced into the upper part of a column packed with Raschig rings and heated to 85°–90°C. 5 m³ (S.T.P.) per hour of air heated to 90°C are introduced hourly at the lower end. The oxime, which has been brought to a water content of 3.8%, is removed from the base of the column. It can be used for rearrangement to caprolactam.

The air which escapes at the head of the column and is charged with water vapor and oxime is now passed into the lower part of a packed condenser through which 200 kg/hour of water are trickled from above. The air which issues retains practically no oxime. The water which issues and initially contains approx. 1,000 ppm of oxime is recycled until it contains approx. 1% of oxime and is then extracted with cyclohexanone to remove the oxime.

EXAMPLE 2

125 parts by volume of cyclohexanone oxime containing 7.2% of moisture are extracted with 50 parts by volume of a concentrated 62 per cent strength hydroxylammonium sulfate solution at a pH of 3.0 at 85°C in the same apparatus as in Example 1. After the extraction, 122 parts by volume of cyclohexanone oxime containing 4.2% of moisture and free even of traces of cyclohexanone are obtained. 3.9 parts by volume of water are distilled from the circulating hydroxylammonium sulfate solution in the distillation column at 85°C and 340 mm Hg.

160 kg per hour of this molten cyclohexanone oxime are treated in countercurrent with 6.5 $Nm^3$ of air which has been heated to 100°C, in a Raschig packed column, as described in Example 1. The oxime which issues contains 2.8% of water. It can be used for rearrangement to caprolactam.

The air which issues from the column and is charged with water vapor and oxime is treated in a packed condenser with 160 kg/hour of a hydroxylammonium sulfate solution which contains approx. 1% of sulfuric acid. The off-air is passed through a cyclone to separate off droplets. The hydroxylammonium sulfate solution can be used as feed for the reaction with cyclohexanone to give cyclohexanone oxime.

EXAMPLE 3

111 parts by volume of cyclohexanone oxime containing 7.0% of water are extracted in countercurrent with 18 parts by volume of a 47 per cent strength ammonium sulfate solution, at 85°C, in the same apparatus as that described in Example 1. The pH of the recycled ammonium sulfate solution assumes a value of 5.4. The cyclohexanone oxime obtained contains 5.0% of water. The content of impurities in the oxime, detectable by gas chromatography, is reduced from 1,690 to 850 ppm. 1.92 parts by volume of water are distilled from the circulating ammonium sulfate solution. 160 kg per hour of this molten cyclohexanone oxime are treated in countercurrent with 8 $m^3$ (S.T.P.) of nitrogen preheated to 90°C, as described in Example 1. The oxime discharged still contains 3.2% of water.

The nitrogen which issues is subsequently washed countercurrent with approx. 300 kg/hour of a 23% strength ammonium sulfate solution.

We claim:

1. A process for the partial dehydration of cyclohexanone oxime by treatment with aqueous solutions of inorganic salts, wherein the crude cyclohexanone oxime is extracted, above its melting point, with a concentrated solution of an ammonium and/or hydroxylammonium salt of a mineral acid in countercurrent in an extraction column and the salt solution is then separated from the partly dehydrated cyclohexanone oxime, re-concentrated by evaporation and recycled to the oxime dehydration process, wherein the cyclohexanone oxime which has been dehydrated to water contents of about 4 to 6% by weight is treated with a heated inert gas above its melting point and the gas is washed to remove entrained cyclohexanone oxime.

2. A process as claimed in claim 1, wherein a concentrated ammonium sulfate solution is used for the dehydration.

3. A process as claimed in claim 1, wherein a concentrated hydroxylammonium sulfate is used for the dehydration.

4. A process as claimed in claim 1, wherein the extractive dehydration is effected at temperatures of from 65°C to the boiling point of the two-phase mixture.

5. A process as claimed in claim 1, wherein the extractive dehydration is effected at a pH of from 3 to 6.

6. A process as claimed in claim 1, wherein the circulating salt solution is reconcentrated in vacuo.

7. A process as claimed in claim 1, wherein the treatment of the cyclohexanone oxime with the gas is effected in countercurrent.

8. A process as claimed in claim 1, wherein the gas is recycled.

9. A process as claimed in claim 1, wherein said salt is selected from the group consisting of ammonium and hydroxylammonium sulfates, chlorides and phosphates.

10. A process as claimed in claim 1 wherein said salt is selected from the group consisting of ammonium sulfate, ammonium chloride, ammonium phosphate and hydroxylammonium sulfate.

* * * * *